(12) United States Patent
Dutta et al.

(10) Patent No.: US 6,326,023 B1
(45) Date of Patent: Dec. 4, 2001

(54) SYNERGISTIC ANTI-MALARIAL FORMULATION

(75) Inventors: Guru Prakash Dutta; Dharam Chand Jain; Ranjendra Singh Bhakuni; Sudhanshu Saxena; Sangeeta Dhawan; Suman Preet Singh Khanuja; Sushil Kumar; Renu Tripathi; Aseem Umesh; Nuzhat Kamal; Anil Kumar Dwivedi; Satyawan Singh, all of Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/537,246

(22) Filed: Mar. 28, 2000

(51) Int. Cl.$^7$ ................................. A61K 9/02; A61K 9/48
(52) U.S. Cl. ........................ 424/436; 424/456; 424/455; 424/452; 514/783; 514/966

(58) Field of Search ..................................... 424/436, 451, 424/455, 456, 452

(56) References Cited

U.S. PATENT DOCUMENTS

| | | | | |
|---|---|---|---|---|
| 5,011,951 | * | 4/1991 | Buchs et al. ......................... | 549/348 |
| 5,219,865 | * | 6/1993 | Chatterjee et al. ................... | 514/305 |

* cited by examiner

Primary Examiner—James M. Spear
(74) Attorney, Agent, or Firm—Ladas & Parry

(57) ABSTRACT

The present invention relates to a synergistic formulation comprising pharmaceutically effective amount of α/β arteether and a neutralized refined vegetable oil suitable for administration by rectal route, method for the treatment of cerebral and comatose malaria and process for the preparation of the said formulation.

28 Claims, No Drawings

SYNERGISTIC ANTI-MALARIAL FORMULATION

FIELD OF INVENTION

The present invention relates to novel synergistic formulation comprising α,β-arteether together with vegetable oil, said formulation useful in the treatment of comatose and cerebral malarial cases. The formulation specifically useful for rectal route treatment of highly multi-drug resistant *P. falciparum* and *P. vivar* cases and which can be used for emergency treatment of comatose and cerebral malaria. The invention also provides methods of treatment of malaria affecting the brain employing the novel formulation. The invention also provides process for preparation of the said novel formulation.

BACKGROUND OF THE INVENTION

According to WHO *P. falciparum* malaria is becoming increasing resistant to chloroquine, sulfadoxine-pyrimethamine and mefloquine (Eyles et al. 1963, Am. J. Torp. Med. Hyg. 12, 840–835; WHO Tech. Report Series No. 711, 1984; Boudreau et al. 1982 Lancet II, 1335; Noreen et al. 1991, Lancet 337, 1140–1143; Hurwitz et al. 1981, Lancet I, 1068–1070; Timmermanns et al 1982, Lancet I 11181).

Although quinine resistance is also emerging along Thailand-Myanmar border, still the quinine and tetracycline combinations remains over 80% effective in practice (Vanijanonta et al. 1992, Lancet 339,369). Besides, seven day regimen of quinine and tetracycline was found to be effective in treating *P. falciparum* cases which were resistant to artesunate, arteether and mefloquine combined therapy.

Mefloquine was reported to produce neuropsychiatric side-effects in adults who developed tonic clonic fits. Besides psychosis, delusions and hallucinations, anxiety sleep disturbances were also reported after mefloquine (Drugs 1990, 39, 160–169).

Multi-drug-resistance in *P. falciparum* malaria and high level of *P. vivax* resistant strains are posing a major threat to countries in South-east Asia. Africa and Southern America. Most seriously affected areas include Thai-Myanmar Burmese border, where resistance to nearly all available drugs (Chlorquine, sulfadoxine-pyrimethamine, mefloquine, quinine) has already got established, (WHO Report on Infectious Diseases, 1999, WHO/CDS/99.1).

Halofantrine is more effective but rather high doses of the drug are now required to control resistant *P. falciparum* Brasseur et al. 1993. Lancet 341, 901–2) which could lead to increased risk of cardiotoxicity of this new antimalarial including sinus bradycardia, sinus arrhythmia, tall peak T. waves, QT interval prolongation, ectopic beats (Karbwang et al. 1993, Lancet, 342, 501; Wildling et al. 1993. Lancet, 342, 55; Kremsner el al. Am. J. Trop. Med. Hyg. 50, 790–795) which has imposed great limitation on the antimalarial potential of this drug. Several reports have recently appeared which document emergence of chloroquine resistance by *P. viva* (Schwartz et al. 1991. New England J. Med. 324, 927; Schuurkamp et al. 1992. Trans. R. Soc. Trop. Med. Hyg. 86, 121–2; Murphy el al., 1993. Lancet, 341, 96–100; Garg et al. 1995. Trans. R. Soc. Trop. Med. Hyg. 89, 656–7; Than et al. 1995. Trans. R. Soc. Trop. Med. Hyg. 89, 307–8; Baird et al., 1996. Trans. R. Soc. Trop. Med. Hyg. 90, 409–410, Baird et al., Am. J. Trop. Med. Hyg. 56, 627–631. The World Health Organization (1984) had accorded high priority to the development of fast acting artemisinin derivatives as blood schizontocides for the emergency treatment of cerebral malaria as well as for the control of multiple drug resistant cases of *Plasmodium falciparum*.

α,β-arteether is an ethylether derivative of qinghaosu (artemisinine), which is extracted from *Artemisia annua*, a plant long known in traditional Chinese medicine for its antimalarial properties. α,β-Arteether (30:70) (intramuscular) is one of the artemisinin derivatives that has been developed in India and shows antimalarial activity against chloroquine, mefloquine and quinine resistant *P. yoelii nigeriensis* and cures experimental cerebral malaria infections (*P. knowlesi/P. fragile* in rhesus monkey model). Dutta et al. 1989. Pharmacol. Res. 21, 415–19; Dutta and Tripathi, 1996, Japn. J. Trop. Med. Hyg. 24, 65–69; Tripathi et al. 1997, Exp. Parasitol. 87, 290–292; Bajpai et al. 1989 Trans. R. Soc. Trop. Med. Hyg. 83, 484).

α,β-Arteether is relatively safer and its $LD_{50}$ dose is 1250 mg/kg in Swiss mice as compared to artemether ($LD_{50}$ 263 mg/kg (im) and artesunate ($LD_{50}$ 475 mg/kg, im)(J. Trad. Chinese Med. 1982,2(1) 31–38). Clinical trials of intramuscular injection of this compound have been completed and marketed. Data on clinical trials with injectable preparation of α,β arteether (30:70 mixtures of isomers amongst *P.falciparum* cases has been published (Mohapatra et al 1996. Indian J. Med. Res. 104, 284–7, Valecha et al. 1997, Int. J. Clin. Pharm. Res. XVII (1)11–15. Mohanty et al. 1997. Trans , R. Soc. Trop. Med. Hyg. 91, 328–330; Mishra et al. 1995, Trans. R. Soc. Trop. Med. Hyg. 89, 299–301).

STATUS OF RECTAL SUPPOSITORIES OF ARTEMISININ DERIVATIVES

Several reports have been published which support the observation that rectal suppository preparations of artemisinin can exert antimalaral effect in reducing the *P. falciparum* parasitaemia in critically sick and and severe cases including cerebral complications (Li et al., Trans.R.Soc-.Trop.Med.Hyg. 88(Suppl 1), 1994, 5–6; Arnold et al., Trans. R.Soc. Trop. Med.Hyg. 84, 1990, 499–502; Hien et al., Trans. R.Soc.Trop.Med. Hyg. 85, 1991, 202–211; Hien et al., Trans. R. Soc. Trop. Med. Hyg. 86, 1992, 582–583; Lie et al., J. Trad. Chinese Med. 5, 1985, 159–161; Cao et al., 1997, Trans.R.Soc.Trop.Med.Hyg. 91, 335–342). The suppository treatment was found satisfactory for parasite clearance and for fever clearance in patients. However, a very high dose of artemisinin (2800 mg in 48–56 h) is needed to be administered to produce complete parasite clearance. Besides the high dose of artemisinin administered may approach the toxicity level and there are frequent problems of recrudescence with this drug in children.

Artesunate suppositories have also been used for control of severe *P. falciparum* cases. Although they produce fast parasite clearance and fever clearance, the recrudescence rate is high. Artesunate suppositories were given at a total dose of 1600 mg (in 8 doses) over 3 day course and in order to prevent recrudescence a long-acting antimalarial mefloquine (1250 mg) was administered to reduce recrudescence rate (92%) [(Looareesuwan et al., Ann.Trop.Med.Parasitol. 89, 1995, 469–475; Looareesuwan et al., Jpn. O. Trop. Med Hyg. 24(suppl 1) 1996, 13–15]. Looareesuwan also administered 1600 mg artesunate suppository which was followed by mefloquine (1250 mg) which produced 96% cure rate and Bhatt et al., [Jpn. J. Trop. Med. Hyg. 24(suppl. 1), 1996, 59–63] also used 1600 mg artesunate suppositories followed by 1000 mg mefloquine. In spite of double treatment 13.6% mortality was recorded (cure rate 86.4%). Gomez [Gomez Landires, Jpn. J. Trop. Med. Hyg. 24 (suppl. 1) 1996, 16–24] employed 1400 mg artesunate suppository which was followed by 750 mg mefloquine. They [Thwe et al., Jpn. J. Trop. Med. Hyg. 24 (suppl. 1) 1996, 25–32] administered 1200 mg artesunate suppositories (in 3 days) followed by 1250 mg mefloquine for treatment of severe malaria and achieved a cure rate of 92.3%. Halpaap et al., (1998, Am. J. Trop. Med. Hyg. 58, 365–368) administered two 50 mg artesunate suppositories at 4 h interval in children followed by sulfadoxin/pyrimethamine, and Sabchareon et al., (1998) administered 200 mg artesunate suppository (x3 days) followed by mefloquine (2 doses).

Most of the trials recommend the administration of a second antimalarial like mefloquine or sulfadoxin/pyrimethamine with artesunate suppository. Wilairatana et al., (1997, Ann. J. Trop.Med. Med.Parasitol 91, 891–896) also reported that artesunate suppository was usefull in reducing and clearing parasitaemia in severe *P. falciparum* cases. Kyaw et al., (1996 Jpn. J. Trop.Med. Hyg. 24 suppl. 1, 55–58) compared the efficacy of artesunate suppositories (200 mg x3 days) and artemether suppositories (200 mgx3 days) and the cure rates among adult uncomplicated falciparum cases were 50 and 43.9% respectively.

Reference is to made to U.S. patent application Ser. No. 09/264,352 filed on Feb. 12, 1999 in respect of formulation of dihydroartemisinin, effective in the control of a wide spectrum of malaria, wherein the Applicants had disclosed formulation comprising an artemisinin derivative. This compound is a lactol derivative of artemisinin obtained from the plant *Artemisia annua* In the said application, the Applicants had formulated DHA capable of being administered by intramuscular, oral and rectal routes. DHA is an intermediate compound which is finally converted into its derivatives α,β-arteethers. The applicants during their study have now found that these compounds can be used for the treatment of malaria.

OBJECTIVES

The main objective of the present invention is to provide a useful synergistic formulation of α,β-arteether for treatment of cerebral malaria.

Another objective of the present invention is to provide a formulation which is highly effective, easy to use, non-messy and non-cumbersome and can be administered by the rectal route to control cerebral malaria and which can also be used to clear a wide spectrum of infections resistant to most of the conventional animals, antibiotic and other drug combinations.

Another objective of the invention is to provide a formulation effective in controlling malarial parasites in both asexual and sexual stages, in both drug sensitive and resistant malaria infections.

Yet another objective is to provide the rectal arteether can be effective in stopping malaria transmission and spread of the disease.

Another objective of the present invention is to give the rectal formulation of arteether in suppositories, as presumptive emergency treatment for comatose malaria cases (both *P. falciparun* and *P. vivax*) to arrest the rising parasitaemia and control infection in blood, which will revive the comatose cases to fill conscious.

Still another objective of the present invention is to provide a process for preparation of rectal formulation usefull for treatment of malaria

SUMMARY OF INVENTION

The present invention relates to a synergistic formulation comprising α/β arteether useful for the treatment of wide spectrum multi-drug resistant malaria and emergency treatment of comatose malaria. The formulation can be administered in malarial cases by rectal route in the form of rectal formulation, suppository in different doses form for infant, children, adults and pregnant woman. The above said formulation can be given by oral route also, for complete elimination of malaria infection. The formulation would be effective in stopping the malarial transmission. The invention also provides a process for the preparation of the said formulation.

DETAILED DESCRIPTION OF THE INVENTION

The invention provides a synergetic formulation comprising pharmaceutically effective amount of α/β arteether and a neutralized refined vegetable oil suitable for administration by rectal route.

In an embodiment, the vegetable oil is sterilized neutral refined oil that does not solidify in winter at room temperature.

In yet another embodiment of the present invention, the ratio of α/β0 arteether and vegetable oil in the formulation is 0.002–0.020:1 w/w, preferably 0,0025:1 w/w.

In still another embodiment, the vegetable oil is selected from the group comprising ground nut oil, sesame oil and tea oil.

In yet another embodiment, α and β tautomers are present in a ratio of 10:90 to 30:70.

In still another embodiment, the preferred ratio of α and β tautomers in the formulation is 30:70.

In an embodiment, the formulation is used against a wide spectrum of *Plasmodium yoelli nigeriensis* (MDR II) parasite resistant to high oral doses of drugs selected from chloroquine, amodoquine, mepacrine, mefloquine, quinine, quinidine, pyrimethamine, pyronaridine, halofantrine, pyrimethamine+sulfadoxin, primaquine and WR 238605.

In still another embodiment, the formulation is used against *Plasmodium yoelii nigeriensis* resistant to antibiotics selected from tetracycline, oxytetracycline, demeclocycline, erythromycin, ciprofloxacine, norfloxacine and doxycycline.

In yet another embodiment, is used against *Plasmodium yoelii nigeriensis* resistant to antimalarial-antibiotic combinational drugs selected from chloroquine+tetracycline, amodiaquine+tetracycline, mefloquine+tectracycline, mepacrine+tetracycline, quinine+tetracycline, quinine+oxytetracycline, quinine+doxycycline, quinine+erythromycin, cyprofloxacine+chloroquine, norfloxacine+chloroquine and quinine+tetracycline.

The said formulation is viscous and light yellow in color.

In still another embodiment, the α and β tautomers in the formulation are present in a ratio of 10:90 to 30:70. and maintains longer half life (22 hrs or more). The same formulation can also be made into regular rectal suppository which can be administered into rectum 3–4 times daily during acute phase of malaria.

In yet another embodiment, the formulation can be used as substitute of primaquine and WR236805 and useful for interrupting transmission of *P. falciparum* because of its gametocytocidal action.

In still another embodiment, the formulation has a half life of about 22 hrs or more.

In yet another embodiment, the formulation provides extended bioavailability because of longer T ½β (clearance) in comparison to other artemisinin derivatives such as artemether or artesunate which have short plasma half life.

In still another embodiment, the formulation shows no adverse gastric effects, hemorrhage etc. which are found in the rectal or oral treatment with other arternisinin derivatives in tablet form.

In yet another embodiment, the formulation is safe ($LD_{50}$>1250 mg/kg), well tolerated and much safer than artemether and artesunate in animal toxicity tests.

In still another embodiment, the formulation can be administered by rectal or oral routes or as gelatin capsule, given three to four times daily, and the formulation has shelf life of more than three years.

In yet another embodiment, the formulation has 100–300 times more accumulation in the malarial infected red blood cells than the normal red blood cells.

In still another embodiment, the said formulation has adequate rectal absorption of compound sufficient to arrest the rising parasitaemia and the treated animals show significant reduction/clearance of parasitaemia indicating sufficient rectal drug absorption.

In yet another embodiment, the formulation has blood schizontocidal activity as useful for the emergency treatment of uncomplicated severe complicated/cerebral and multi-drug resistant malarial infections including comatose malaria cases (for which it is the first line of emergency treatment).

The said formulation has no adverse met-hemoglobin type of toxicity which is known to be associated with administration of primaquine and WR36805.

In one more embodiment, the invention provides methods for the treatment of comatose cerebral malarial conditions comprising the steps of rectal administration of the formulation to a subject in need thereof.

In still another embodiment, which can be administered through intra-recta or oral route or primarily by intra rectal followed by oral route.

In yet another embodiment, wherein the formulation is effective against sexual stage of parasites selected from *P. falciparum, P. vivac* and *P. cynomolgi*.

In still another embodiment, wherein the formulation is effective at much lower dose as gametocytocide compared to dose required for treatment of asexual blood stages.

In yet another embodiment, the formulation for rectal/oral treatment is used in the form of rectal formulation/ rectal suppositories/ oral gelatin capsules of liquid formulations in different dose forms for infants, children and adults.

In still another embodiment, the formulation is effective and safe in pregnant malaria infected monkeys, and could be useful for treatment of severe malaria in pregnant women.

In yet another embodiment, the formulation is administered by the rectal route in children as well as adults for longer periods of once or twice a week until transmission continues.

In one more embodiment, the process for the preparation of a formulation useful for the control of wide spectrum of malaria comprising (a) preparation of arteether α and β from artemisinin by known methods, (b) dissolving α/β arteether in sterilized neutral refined vegetable oil heating at 70–90° C. for 2–4 min. and (c) cooling the solution at room temperature to obtain the desired formulation and (d) followed by sterilization of formulation by filtration through 0.45 μm filter.

NOVELTY OF THE INVENTION

The major advantage of the arteether rectal formulation will be to treat very serious cases/comatose cases of cerebral malaria with a view to reduce mortality among *P. falciparum* cases particularly in children, pregnant women who are at maximum risk and can prove fatal unless the emergency therapy is instituted.

A still another advantage of the rectal formulation of arteether will be to control multi-drug resistant infections due primarily to *P. falciparum* which because of problem of resistance can not be treated effectively or cured with conventional antimalarial drugs such as chloroquine, mefloquine, amodiaquine, mepacrine, quinine, quinidine, halofantrin, pyrimethhamine, pyronaridine, W38605 to which the parasite might be resistant, or with standard suppressive antimalarial antibiotics such as tetracycline, oxytetracycline, demeclocycline, doxycycline, erythromycin, ciprofloxacin, norfloxacin to which plasmodia may be resistant or with diverse antimalarial+antibiotic combination such as chloroquine, amodiquine/mefloquine/mepacrine/quinine/quinidine+tetracycline combinations or quinine/quinidine+oxytetracycline combination, or quinine+erythromycin or ciprofloxacin+chloroquine combination, or norfloxacin+chloroquine combination against which the *P. falciparum* infection is resistant.

Another advantage of formulation will be to control chloroquine resistant *P. vivax* blood infections which are presently spreading in many continents could be effectively treated initially with rectal arteether formulation to prevent deterioration of the condition of the patient, and as soon as the patient is brought to the hospital arteether formulation can also be given parenterally as intramuscular (3 doses) curative treatment.

All cases of *P. falciparum* and *P. vivax* which need a life saving therapy/those in coma/serious complicated *P. falciparum* infections/life threatening malaria including children, infants can be administered rectal arteether formulations 2–4 times daily to revive the comatose cases and rectal therapy used as emergency treatment can be changed to parenteral (oral) therapy with same arteether formulation (prepared in neutralized oil) which allows rapid drug absorption from gut and can provide effective control of parasitaemia, by oral route.

The advantages of these formulations as prepared by the process of the present invention are that they provide a highly effective, easy to use, non messy and non cumbersome rectal delivery system to control cerebral malaria and which can also be used to clear highly multi-resistant malaria infections.

Rectal suppositories are simple to administer, easy to store at room temperature and administered, as it does not require any special equipment and can be given as emergency drug at rural health centers throughout the developing world. Suppository could be used in remote areas/villages incases who might not survive the long journey or delay in reporting to the hospital.

The formulation ($\alpha/\beta$-arteether and vehicle) is relatively safe as compared to other artemisinin derivatives ($LD_{50}$ in mice>1250 mgfkg) and consequently the therapeutic index is more favorable for treatment of malaria.

The neutralized refined oil thus prepared was superior to commercial refined oil because it was stable even during winter on the shelf and did not solidify during overnight very low temperature.

Accordingly, the present invention provides a process of the preparation of formulation useful for treatment of malaria, which comprises mixing 5 to 15% by weight of arteether with 85 to 95% by weight of neutralized refined ground nut oil which can be put into soft gelatin capsule for rectal treatment, or taking material in syringe and giving rectal administration of drug through a nozzle or catheter or prepare into standard suppository by known methods.

In an embodiment of the present invention, $\alpha/\beta$ arteether used may be selected from the mixture in different proportions ranging from 10–30 of $\alpha$- and 70–90 of $\beta$-isomers.

In yet another embodiment of the present invention the formulation used may be mixed with known suppository formulations such as glycerols substituted glycol, alkyl alcohol and mixture thereof. The resulting composition (formulation and standard suppository materials) may be molded into desired shape and size. The composition can also be made into a suppository like glycrine suppository or can be put in a soft gelatin capsule or the final formulations can be administered deep into rectum through plastic nozzle or rubber catheter 2–4 times daily for several days to reduce the parasitaemia to eliminate infection.

The following example broadly illustrate the nature of this invention the manner in which it is to be performed without limiting the nature and scope of the invention.

Arteether Formulation

Preparation of Neutralized Oil for the Formulation (a) Neutralized oil: Refined ground nut oil was purchased from commercial source locally. 100 ml oil was taken in separating funnel and to this 50 ml of sterile 5% sodium bicarbonate solution was added and was shaken for 10 min thoroughly to mix sodium bicarbonate with the oil. This solution was allowed to stand for 2 hrs, sodium bicarbonate layer was drawn out and fresh bicarbonate was added and process was repeated for 4 times to prepare neutralized oil. Last bicarbonate washing was continued for over night and after bicarbonate treatment, washing with sterilized deionized distilled water was started and likewise 4 washing of the treated oil were given with 50 ml distilled water. After the last washing, oil was filtered through double layered Whattman filter no. 3, the filtration process was continued over night and neutralized oil was collected. The neutralized oil thus obtained was passed through $2^{nd}$ set of Whattman filter paper to obtain moisture free clear neutralized oil. The washed neutralized oil was put in sterilized flask and it was heated on hot plate to 140° C. for 1 hr. The oil was aseptically dispensed in glass stopped bottle to avoid aeration/oxidation. This oil could be stored at room temperature on the shelf as light yellowish coloured liquid. This neutralized oil is used for preparation of rectal formulation.

(b) Preparation of rectal arteether formulation: Stock solution of the drug $\alpha/\beta$ arteether (30:70) mixture of enantiomers $\alpha$ and $\beta$ respectively, was prepared in neutralized refined ground nut oil. Arteether $\alpha$ and $\beta$ were finally dissolved in neutralized ground nut oil to get the desired drug solution for administration. The mixture was heated to 70–90° C. to dissolve the arteether and the final drug solution was filtered through 0.45 $\mu$millipore filter. The arteether preparation is of light yellowish colour and is stable for over 3 years. For animal experiments various dose level of drug arteether can be made by dilution of the drug stock with neutralized oil vehicle. The arteether formulation can be used for preparing rectal formulation and can also be administered orally to achieve curative action.

(c) Method for the Preparation of suppository: A mixture of polyethylene glycol (PEG Mol. Wt. 1500), 350 mg, polyethylene glycol (Mol. Wt. 4000) 150 mg and hexane-1-ol (0.1 ml) was melted by heating on a water bath and 150 mg of $\alpha/\beta$-arteether in two ml of hexane was added to it with intimate mixing. The hexane was evaporated off by warming the mixture to 60° C. and the mixture was allowed to cool to get solid mass which was molded into suppositories of oval shape and 1×1×0.5 cm size. It was then packed in a polyethylene lined blister type packing to avoid coming into contact with moisture before use. Besides other known suppository materials can be used to prepare the formulation.

Biological Activity

Examples 1

Multi-drug Resistant Character of *Plasmodum voelli niaeriensis*(MDR Strain)

Swiss mice weighing 20±1 to 25±g of either sex and random laboratory bred at Central Drug Research Institute, Lucknow were used. Mice were routinely infected with $1\times10^5$ parasitized RBC intraperitoneally using sterile citrate saline as diluent for infected blood. The parasite suspension were inoculated in healthy mice by intraperitoneal route on day 0, and drugs were administered orally once a day for 4 doses (day 0 to day +3). From day 4 onwards, tail blood smears were examined after Giemsa staining and percent parasitaemia and mortality was recorded. The parasite (MDR strain) was lethal for Swiss mice and mice died in 6–8 days after developing parasitaemia above 40% to 100% infection of RBC, Mortality was 100% in mice.

parasitaemia (57.6±24.7) and had starting dying whereas the groups of mice administered 15–20 mg/kg α,β-arteether formulation by rectal route treatment were fully protected as shown by negative parasitaemia. The study shows fairly rapid drug absorption of this formulation by rectal route which was effective in initially controlling multi-drug resis-

TABLE

Present status of resistance pattern of *P. yoelii nigeriensis* (MDR II) strain to different antimalarials in Swiss mice.

| Drug/antibiotics | Dose mg/kg (Oral) × days | Parasite response | Drug | Dose mg/kg (Oral) × days | Parasite response |
|---|---|---|---|---|---|
| Chloroquine | 128 × 4 | Resistant | Chloroquine + Tetracycline | 128 × 4 / 250 × 4 | Resistant |
| Amodiaquine | 128 × 4 | Resistant | Amodiaquine + Tetracycline | 128 × 4 / 250 × 7 | Resistant |
| Mefloquine | 128 × 4 | Resistant | Mefloquine + Tetracycline | 128 × 4 / 250 × 7 | Resistant |
| Mepacrine | 128 × 4 | Resistant | Mepacrine + Tetracycline | 128 × 4 / 250 × 4 | Resistant |
| Quinine | 400 × 4 | Resistant | Quinine + Tetracycline | 300 × 4 / 500 × 4 | Resistant |
| Quinidine | 400 × 4 | Resistant | Quinine + Oxytetracycline | 300 × 4 / 500 × 4 | Resistant |
| Halofantrine | 32 × 4 | Resistant | Quinine + Doxycyline | 300 × 4 / 25 × 4 | Resistant |
| Pyrimethamine | 16 × 4 | Resistant | Quinine + Erythromycin | 300 × 4 / 250 × 4 | Resistant |
| WR238605 | 10 × 7 | Resistant | | | |
| Tetracycline | 500 × 4 | Resistant | Ciprofloxacine + Chloroquine | 50 × 4 / 32 × 4 | Resistant |
| Oxytetracycline | 500 × 4 | Resistant | Norfloxacine + Chloroquine | 50 × 4 / 32 × 4 | Resistant |
| Demeclocycline | 500 × 4 | Resistant | | | |
| Doxycycline | 25 × 4 | Resistant | Quinidine + Tetracycline | 400 × 4 / 250 × 4 | Resistant |
| Erythromycin | 250 × 4 | Resistant | | | |
| Ciprofloxacine | 50 × 4 | Resistant | | | |
| Norfloxacine | 50 × 4 | Resistant | | | |

Example 2

Rectal Formulation of α/β Arteether

α,β-Arteether mixture dissolved in neutralized groundnut oil was administered to *P. yoelli nigeriewis* (MDR II) infected mice at 10 mg/kg to 20 mg/kg dose from day 0 to day 2 (for 3 consecutive days) by intra-rectal route. Drug was administered with 0.05–0.25 ml oil (vehicle) in single dose or in 2 divided dose daily. Parasitaemia was recorded daily from tail blood smears stained with Giemsa stain and results are given as % parasitaemia (means±SD). All the doses of arteether namely 10.0, 15.0 and 20.0 mg/kg suppressed the parasitaemia even after treatment (upto 5 days) as shown by blood smear examination. The study shows that till day 5, the control mice had developed very high level of tant (II) *P. yoelli nigeriensis* infection in mice. Presumptive arteether rectal formulation or suppository administration can save mortality in severe/complicated cases. α/β Arteether rectal route controls the severity of infection and prevents mortality in severe complicated comatose malaria cases and will be specially useful in infants, children and those having frequent vomiting and can not be given oral formulation initially. Rectal formulation can easily control highly multi drug resistant malaria infections which do not respond to drugs like chloroquine, amodiaquine, mepacrine, mefloquine, halofantrine, quinine, quinidine, pyrimetharne +sulfadoxin etc. in MDR areas. Rectal route α/β arteether formulation remains $1^{st}$ line of emergency treatment of comatose *P. falciparum* cases in areas of MDR.

TABLE

Blood schizontocidal action of arteether α/β formulation on multi-resistant *P. yoelli nigeriensis* (MDR II) infection in Swiss mice (25 ± 1 g) by rectal route of administration.

| Treatment route | Dose mg/kg × days | Parasitaemia % (mean ± SD) | | | |
|---|---|---|---|---|---|
| | | Day 4 | Day 5 | Day 11 | Day 28 |
| α/β arteether (rectal) | 10 × 3 | 0.0002 ± 0.001 (8)6-ve | 0.002 ± 0.080 (8)6-eve | 0.0 (3) | 0.0 (3) |

TABLE-continued

Blood schizontocidal action of arteether α/β formulation on multi-resistant
*P. yoelli nigeriensis* (MDR II) infection in Swiss mice (25 ± 1 g) by rectal route of administration.

| Treatment route | Dose mg/kg × days | Parasitaemia % (mean ± SD) | | | |
|---|---|---|---|---|---|
| | | Day 4 | Day 5 | Day 11 | Day 28 |
| | 10 × 3* | 0.0 (8) | 0.0 (8) | 10.25 ± 10.0 (4) | 0.0 (1) |
| | 15 × 3 | 0.0 (8) | 0.0 (8) | 0.0 (4) | 0.0 (4) |
| | 15 × 3* | 0.0 (8) | 0.0 (8) | 0.0 (4) | 0.0 (4) |
| | 20 × 3 | 0.0 (8) | 0.0 (8) | 0.0 (5) | 0.0 (5) |
| | 20 × 3* | 0.0 (8) | 0.0 (8) | 0.0 (6) | 0.0 (6) |
| Control | — | 21.85 ± 24.3 (7) | 57.6 ± 24.7 (5) | Died on day 7 | |

*The dose was given in 2 divided doses at 6 hrs intervals. Number of animals given in parenthesis.

EXAMPLE 3

Oral Use of Formulation

3a). Blood Schizonticidal Activity of Orally Administered Arteether Formulation prepared in DMSO-distilled Water Against MDRII *P. voelii nigeriensis* infection in Swiss Mice (25±1 g)

Swiss mice 25±1 gm infected intraperitoneally with $1 \times 10^7$ parasitized rbcs were administered α/β formulation, prepared in DMSO (3–4 drop) and then suspended in distilled water by oral administration at various doses ranging between 40–100 mg/kg for 5 consecutive days.

Parasitaemia was recorded periodically from tail blood smears upto 28 days of observation. Both 60 and 80 mg/kg×5 doses were able to eliminate the prasitaemia upto 28 days of observation and were curative. The 40 mg/kg dose provided transient suppression of parasitaemia, but was not curative against MDR strain. A very high dose is required for curative action against MDR of infection and its bioavailability by oral route as suspension in D.W. is low.

given once daily for five consecutive days (starting from day 0 to day 4). Blood smears made from tail blood and stained with giemsa were examined periodically till 28 days of infection to record parasitaemia levels and number of surviving/cured mice till 28 days. The results set in table show that the arteether formulation (in neutralized refined ground nut oil) was curative (8/8) in 5 day treatment schedule at 30 mg/kg dose schedule. Both 15 and 20 mg/kg doses cleared the parisitaemia for 6–7 day but there was recrudescence later even though 4–5 mice out of 8 mice (treated in group) showed complete parasite clearance by day 28. Data show adequate drug absorption after oral use of the formulation in neutralized oil and ultimate control of highly multi drug resistant malaria infection (*P. yoelii nigeriensis* MDR II) was achieved.

As discussed above the bioavailability of oral arteether α/β (powder) prepared into dosage form in DMSO and Blood schizonticidal activity of oral α/β arteether formulation against *P. yoelli nigeriensis* Parasitaemia %

| Treatment | Dose | Day 4 | Day 7 | Day 10 | Day 14 | Day 21 | Day 28 |
|---|---|---|---|---|---|---|---|
| α/β arteether | 40 mg/kg × 5 | Nil | Nil | 3.86 ± 7.98 | 3.5 ± 8.5 | Nil | Nil |
| (oral route) | 60 mg/kg × 5 | Nil | Nil | Nil | Nil | Nil | Nil |
| in DMSO- | 80 mg/kg × 5 | Nil | Nil | Nil | Nil | Nil | Nil |
| distilled water | 100 mg/kg × 5 | Nil | Nil | Nil | Nil | Nil | Nil |
| Control | | 26.55 ± 14.43 | 6.4 ± 0.0 | 28.0 ± 0.0 | 6.4 ± 0.0 | | |

Curative dose = 60 mg/kg × 5 doses

3b). Oral Administration of Arteether Formulation (in Oil)

Efficacy of oral administration of arteether formulation for control of blood induced multi-drug resistant *P. yoebi nigerensis* (MDR II) in Swiss mice (25±g) was evaluated. The mice was infected intraperitoneafly with $1 \times 10^5$ parasitized RBC, and drug treatment 10,15,20 and 30 mg/kg was distilled water is of lower order and a dose of 60 mg/kg×5 days is needed for multi-drug resistant *P. yoelii nigeriensis* (MDRII) total clearance, whereas oral arteether (α/β) formulation in neutralized refined ground nut oil is much more effective and 50% drug dose (30 mg/kg×5) is effective in 100% parasite clearance. Thus formulation in oil is superior for treatment of malaria

TABLE

Blood schizonticidal activity of α/β arteether formulation in neutralized oil by oral route against *P. yoelii nigeriensis* (MDR II) in Swiss mice.

| Treatment (Route) | Dose mg/kg × days | No. of mice | % Parasitaemia (mean ± SD) | | | | |
|---|---|---|---|---|---|---|---|
| | | | Day 6 | Day 9 | Day 12 | Day 14 | Day 28 |
| α/β arteether (oral route) | 10 × 5 | 8 | 0.9 ± 1.0 | 41 ± 32.8 | 0.0 (2) | 0.0 (2) | 0.0 (2) |
| | 15 × 5 | 8 | 0.0 | 5.12 ± 5.7 | 0.0 (4) | 0.0 (4) | 0.0 (4) |
| | 20 × 5 | 8 | 0.0 | 3.75 ± 10.6 | 18.8 ± 32.5 | 0.0 (5) | 0.0 (5) |
| | 30 × 5 | 8 | 0.0 | 0.0 | 0.0 | 0.0 (8) | 0.0 (8) |
| Control (vehicle) | 0.5 ml arachis oil | 8 | 74 ± 19.8 | Died | | | |
| Control | | 8 | 66.5 ± 23.4 | Died | | | |

Number of mice surviving are shown in parenthesis.

EXAMPLE 4

4. Transmission Blocking Activity of α/β Areether Formulation in Clinical Malaria Case (*P. falciparum*)

*P. faiciparzum* clinical cases (no=8) which were ganetocyte carriers were administered arteether formulation parenterally (intramuscular) at 150 mg dose (in neutralized ground nut oil)×3 days for treatment of malaria, and within 48 h both asexual parasitaemia and gametocytes were completely cleared from the blood stream. Out of 8 cases, 7 cases were cleared of gamerocytes 24 h of treatment while in the 8$^{th}$ case gametocytes were cleared by 48 h. The study shows strong gametocytocidal action of arteether formulation. All cases remained parasite free upto 28 days observation and drug cure rate was 100 percent. For control and total clearance of asexual parasites arteether 150 mg/kg×3 days treatment is necessary but to achieve gametocyte clearance even one dose (150 mg/kg/60 kg adult) may be given once a week or maximum twice a week to knock out *P. falciparum* gametocytes.

What is claimed is:

1. A formulation comprising α/β arteether and a neutralized refined vegetable oil in respective amounts effective to provide for rectal absorption of the formulation in a patient to be treated sufficient to achieve a synergistic result in treating a multi-drug resistant malarial infection in the patient.

2. A formulation as claimed in claim 1, wherein the vegetable oil is sterilized neutral refined oil that does not solidify in winter at room temperature.

3. A formulation as claimed in claim 1, wherein the ratio of the α/βarteether and the vegetable oil in the formulation is 0.002–0.020:1 w/w.

4. A formulation as claimed in claim 1, wherein the ratio of the α/β arteether and the vegetable oil in the formulation is about 0.002–0.0025:1 w/w.

5. A formulation as claimed in claim 1, wherein the vegetable oil is selected from the group consisting of ground nut oil, sesame oil and tea oil.

6. A formulation as claimed in claim 1, wherein α/β tautomers are present in the α/β arteether in a ratio of 10:90 to 30:70.

TABLE

Blood schizontocidal and gametocytocidal effect of α/β arteether formulation based on gametocyte and asexual parasite clearance rate in *P. falciparum* cases

| Treatment route | Dose | S. No. | Parasitaemia (%) | | Asexual parasitaemia/ gametocytaemia at | |
|---|---|---|---|---|---|---|
| | | | before treatment | | 24 hr | 48 hr |
| Arteether formulation (intramuscular) | 150 mg × 3 days | 1 | Asexual | 0.05% | Nil | |
| | | | Gametocyte | 0.26% | Nil | |
| | | 2 | Asexual | 0.025% | Nil | |
| | | | Gametocyte | 0.012% | Nil | |
| | | 3 | Asexual | 0.7% | 0.016% | Nil |
| | | | Gametocyte | 0.07% | 0.01% | Nil |
| | | 4 | Asexual | 0.01% | Nil | |
| | | | Gametocyte | 0.003% | Nil | |
| | | 5 | Asexual | 0.033% | Nil | |
| | | | Gametocyte | 0.013% | Nil | |
| | | 6 | Asexual | 0.50% | Nil | |
| | | | Gametocyte | 0.05% | Nil | |
| | | 7 | Asexual | 0.02% | Nil | |
| | | | Gametocyte | 0.025% | Nil | |
| | | 8 | Asexual | 0.5% | 0.01% | Nil |
| | | | Gametocyte | 0.001% | Nil | |

7. A formulation as claimed in claim wherein the ratio of the α and β tautomers in the formulation is about 30:70.

8. A method for treating a patient infected with a *Plasmodium yoelii nigeriensis* (MDR II) parasite resistant to high oral doses of drugs selected from the group consisting of chloroquine, amodoquine, mepacrine, mefloquinine, quindine, pyrimethamine, pyronaridine, halofantrine, pyrimethamine+sulfadoxin, primaquine and WR238605, said method comprising treating the patient by administering the formulation of claim 1 the patient.

9. A method for treating a patient infected with a *Plasmodium yoelii nigeriensis* parasite resistant to antibiotics selected from the group consisting of tetracycline, oxytetracycline, demeclocycline, erythromycin, ciprofloxacine, norfloxacine and doxycycline, said method comprising treating the patient by administering the formulation of claim 1 to the patient.

10. A method for treating a patient infected with a *Plasmodium yoelii nigeriensis* parasite resistant to antimalarial-antibiotic combinational drugs selected from the group consisting of chloroquine+tetracycline, amodiaquine+tetracycline, mefloquine+tetracycline, mepacrine+tetracycline, quinine+tetracycline, quinine+oxytetracyclinie, quinine+doxycycine, quinine+erythromycin, cyprofloxacine+clhloroquinie, norfloxacine+chloroquine and quinine+tetracycline, the method comprising treating the patient by administering the formulation of claim 1 to the patient.

11. A formulation as claimed in claim 1, wherein the formulation is viscous and light yellow in color.

12. A formulation as claimed in claim 1, wherein α and β tautomers are present in the α/β arteether in a ratio which provides the α/β arteether with a half life of 22 hours or more.

13. A formulation as claimed in claim 1 which is encapsulated in a gelatin capsule.

14. A method for the treatment of comatose cerebral malarial conditions comprising the step of rectal administration of the formulation of claim 1 to a subject in need thereof.

15. A method as claimed in claim 14, wherein the formulation is administered 3–4 times daily to the subject.

16. A method for treating comatose cerebral malarial conditions in a patient comprising administering the formulation of claim 1 to the patient.

17. A method as claimed in claim 16, wherein the patient is infected with parasites selected from the group consisting of *P. falciparum, P vivax* and *P. cynomolgi,* said parasites being in a sexual stage.

18. A method as claimed in claim 16, wherein the formulation is administered to the patient in the form of a rectal formulation, a rectal suppository or an oral gelatin capsule.

19. A method as claimed in claim 16, wherein the patient is a pregnant woman with severe malaria.

20. A method as claimed in claim 16, wherein the patient is a child.

21. A process for the preparation of a composition useful for the control of malaria comprising (a) preparing arteether α and β from artemisinin; (b) dissolving the α/β arteether in a sterilized neutral refined vegetable oil with heating at 70–90° C. for 2–4 minutes; (c) cooling the solution formed in step (c) at room temperature to obtain a formulation and (d) sterilizing the formulation by filtration through a filter.

22. A process as claimed in claim 21, wherein the filter is a 0.45 μm filter.

23. A process for the preparation of the formulation as claimed in claim 1, comprising mixing 5 to 15% by weight of arteether with 85–95% by weight of neutralized refined ground nut oil.

24. A process as claimed in claim 23 comprising encapsulating the formulation in a soft gelatin capsule for rectal treatment.

25. A process as claimed in claim 23 comprising inserting the formulation into a suppository.

26. A process as claimed in claim 23, wherein the arteether is selected from α/β arteether in a ratio of 10–30 of α- and 70–90 of β-isomers.

27. A process as claimed in claim 21, wherein the formulation is mixed with a suppository formulation.

28. A method for treating a patient having blood schizontocidal activity as useful for the emergency treatment of cerebral and multi resistant malarial infections, including comatose malaria cases, said method comprising treating the patient by administering the formulation of claim 1 to the patient.

* * * * *